(12) United States Patent
Tanaka et al.

(10) Patent No.: US 11,385,431 B2
(45) Date of Patent: Jul. 12, 2022

(54) OPTICAL FIBER CORE WIRE

(71) Applicant: MITSUBISHI CABLE INDUSTRIES, LTD., Tokyo (JP)

(72) Inventors: Masatoshi Tanaka, Amagasaki (JP); Yoshiki Yamakawa, Amagasaki (JP); Hideaki Itou, Amagasaki (JP); Daiki Tabei, Amagasaki (JP)

(73) Assignee: Mitshishi Cable Industries, Ltd., Tokyo (JP)

( * ) Notice: Subject to any disclaimer, the term of this patent is extended or adjusted under 35 U.S.C. 154(b) by 0 days.

(21) Appl. No.: 16/474,504

(22) PCT Filed: Dec. 12, 2017

(86) PCT No.: PCT/JP2017/044495
§ 371 (c)(1),
(2) Date: Jun. 27, 2019

(87) PCT Pub. No.: WO2018/123556
PCT Pub. Date: Jul. 5, 2018

(65) Prior Publication Data
US 2019/0346649 A1 Nov. 14, 2019

(30) Foreign Application Priority Data
Dec. 27, 2016 (JP) .............................. JP2016-252795

(51) Int. Cl.
*G02B 6/44* (2006.01)
*A61B 1/00* (2006.01)
(Continued)

(52) U.S. Cl.
CPC .......... *G02B 6/4478* (2013.01); *A61B 1/0017* (2013.01); *A61B 18/26* (2013.01);
(Continued)

(58) Field of Classification Search
None
See application file for complete search history.

(56) References Cited

U.S. PATENT DOCUMENTS 5,182,785 A * 1/1993 Savegh ................ G02B 6/4458
385/128
5,644,670 A * 7/1997 Fukuda .............. G02B 6/02038
385/124
(Continued)

FOREIGN PATENT DOCUMENTS

JP H04-066905 A 3/1992
JP H07-503079 A 3/1995
(Continued)

OTHER PUBLICATIONS

International Search Report for PCT Application No. PCT/JP2017/044495, dated Mar. 13, 2018 in 4 pages.

*Primary Examiner* — Chris H Chu
(74) *Attorney, Agent, or Firm* — Knobbe, Martens, Olson & Bear, LLP

(57) ABSTRACT

The coated optical fiber (10) includes: an optical fiber (11) including a core (111) and a cladding (112); a first buffer layer (121) covering the optical fiber (11), and having a refractive index lower than that of the cladding (112) and a Shore D hardness of D/20.0/1 or higher; a second buffer layer (122) covering the first buffer layer (121), and having a higher Shore D hardness than the first buffer layer (121); and a jacket (13) covering the second buffer layer (122).

7 Claims, 2 Drawing Sheets

(51) Int. Cl.
*A61B 18/26* (2006.01)
*A61B 18/22* (2006.01)

(52) U.S. Cl.
CPC ............. *A61B 2018/2222* (2013.01); *A61B 2018/2244* (2013.01)

(56) References Cited

U.S. PATENT DOCUMENTS

| | | | | |
|---|---|---|---|---|
| 5,748,826 | A * | 5/1998 | Nagano | G02B 6/02395 |
| | | | | 385/126 |
| 5,857,761 | A * | 1/1999 | Abe | G02B 6/001 |
| | | | | 362/551 |
| 5,966,490 | A * | 10/1999 | Minns | G02B 6/02033 |
| | | | | 385/123 |
| 2003/0099451 | A1* | 5/2003 | Walker, Jr. | C03C 25/106 |
| | | | | 385/128 |
| 2008/0008432 | A1* | 1/2008 | Dragic | H01S 3/06716 |
| | | | | 385/127 |
| 2009/0087154 | A1* | 4/2009 | Bradley | G02B 6/4401 |
| | | | | 385/113 |
| 2011/0085772 | A1 | 4/2011 | Benjamin et al. | |
| 2011/0150403 | A1* | 6/2011 | Kachmar | G02B 6/4433 |
| | | | | 385/103 |
| 2017/0139129 | A1* | 5/2017 | Luo | C03B 37/01217 |

FOREIGN PATENT DOCUMENTS

| | | |
|---|---|---|
| JP | H08-194139 A | 7/1996 |
| JP | 2000-510609 A | 8/2000 |
| JP | 2005-505013 A | 2/2005 |
| JP | 2016-110009 A | 6/2016 |

* cited by examiner

OPTICAL FIBER CORE WIRE

CROSS-REFERENCE TO RELATED APPLICATIONS

This application is the U.S. National Phase under 35. U.S.C. § 371 of International Application PCT/JP2017/044495, filed Dec. 12, 2017, which claims priority to Japanese Patent Application No. 2016-252795, filed Dec. 27, 2016.

TECHNICAL FIELD

The present invention relates to an optical fiber core wire (hereinafter referred to as coated optical fiber).

BACKGROUND ART

A coated optical fiber obtained by coating an optical fiber with a plurality of resin layers is known. For example, Patent Document 1 discloses a coated optical fiber obtained by coating an optical fiber of quartz with a first coating layer and a second coating layer. The first coating layer is an inner layer made of a urethane acrylate resin with low hardness. The second coating layer is an outer layer made of a urethane acrylate resin with high hardness. Patent Document 2 discloses a coated optical fiber obtained by coating a polymer clad optical fiber with a first coating layer and a second coating layer. The first coating layer is an inner layer made of a thermosetting silicone resin composition with a perfluoro ether polymer structure. The first coating layer is an inner layer made of a thermosetting silicone resin composition.

CITATION LIST

Patent Documents

Patent Document 1: Japanese Unexamined Patent Publication No. H8-194139
Patent Document 2: Japanese Unexamined Patent Publication No. 2016-110009

SUMMARY OF THE INVENTION

The present invention is directed to a coated optical fiber including: an optical fiber including a core, and a cladding covering the core and having a refractive index lower than a refractive index of the core; a first buffer layer covering the optical fiber, and having a refractive index lower than the refractive index of the cladding and a Shore D hardness of D/20.0/1 or higher; a second buffer layer covering the first buffer layer, and having a Shore D hardness higher than the Shore D hardness of the first buffer layer; and a jacket covering the second buffer layer.

DESCRIPTION OF EMBODIMENT

Figure 1:
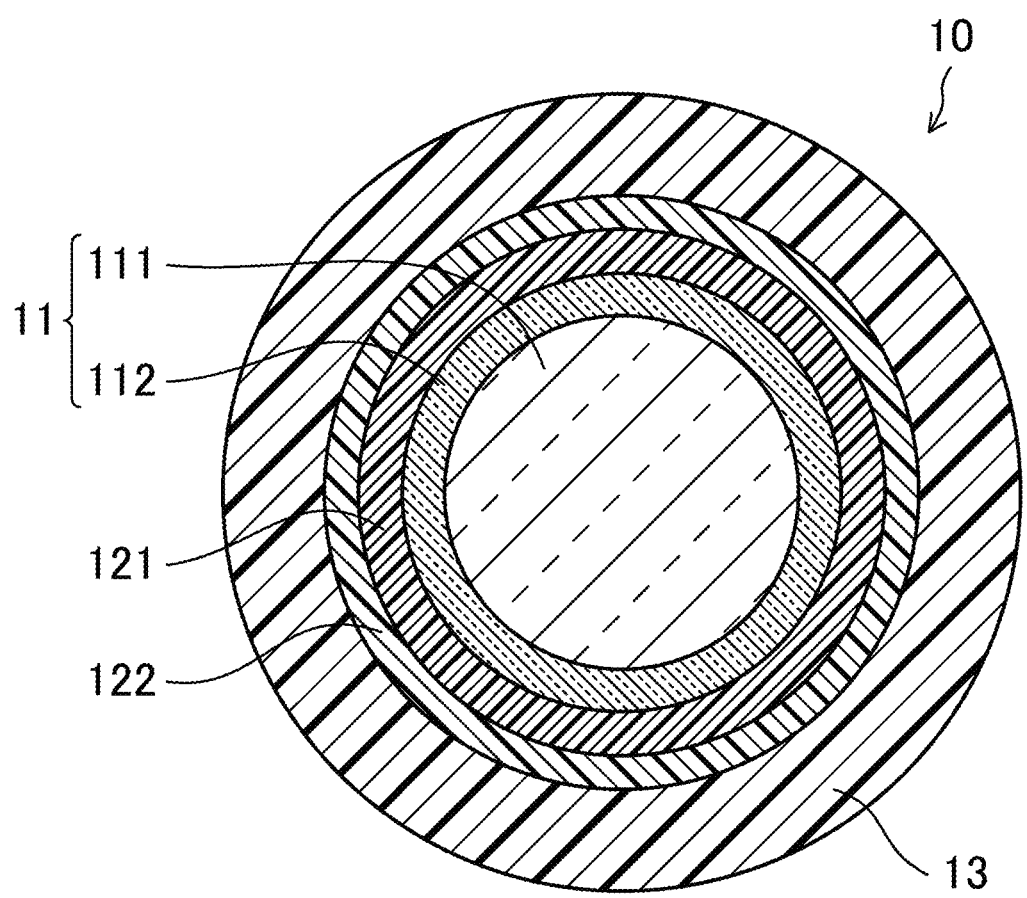
FIG. 1 is a cross-sectional view of a coated optical fiber according to an embodiment.

An embodiment will be described in detail below.
FIG. 1 illustrates a coated optical fiber 10 according to the embodiment. The coated optical fiber 10according to the embodiment is used for, for example, an endoscope device for treatment for a urinary or kidney stone to crush by irradiation with a laser beam.

The coated optical fiber 10 according to the embodiment includes an optical fiber 11, a first buffer layer 121, a second buffer layer 122, and a jacket 13. The optical fiber 11 includes a core 111 and a cladding 112. In the coated optical fiber 10 according to the embodiment, the core 111 and the cladding 112 of the optical fiber 11, the first and second buffer layers 121 and 122, and the jacket 13 are concentrically provided. With the structure described below, the coated optical fiber 10 exhibits a low bending loss when being bent with a small bending diameter, and excellent removability of the jacket 13. The coated optical fiber 10 has an outer diameter, for example, within a range from 0.25 mm to 1.5 mm. The optical fiber 11 has an outer diameter, for example, within a range from 0.15 mm to 1.0 mm.

The core 111 of the optical fiber 11 is provided at the center of the fiber. The core 111 is made of quartz in one preferred embodiment. The core 111 may be made of pure quartz, or quartz doped with a dopant, such as germanium, increasing the refractive index.

The core 111 generally has a circular cross-section with a diameter, for example, within a range from 130 µm to 950 µm. The refractive index of the core 111 is higher than that of the cladding 112, which will be described later, and falls, for example, within a range from 1.458 to 1.502. The refractive index here is measured using light with a wavelength of 589 nm (i.e., a d-line) at a temperature of 25° C. (hereinafter, the same).

The cladding 112 of the optical fiber 11 is, like a layer, provided directly on and integral with the core 111 to cover the core 111. If the core 111 is made of pure quartz, the cladding 112 is made of quartz doped with a dopant, such as fluorine, decreasing the refractive index in one preferred embodiment. If the core 111 is higher in refractive index than pure quartz, the cladding 112 may be made of pure quartz.

The cladding 112 has a thickness, for example, within a range from 5.0 µm to 50 µm. The refractive index of the cladding 112 is lower than that of the core 111, and falls, for example, within a range from 1.430 to 1.458. The difference in the relative refractive index between the core 111 and the cladding 112 falls, for example, within a range from 0.70% to 4.0%. The difference in the relative refractive index here is obtained as follows in percentage. The refractive index of the cladding 112 is subtracted from the refractive index of the core 111. The difference is then divided by the refractive index of the core 111. The obtained value is multiplied by 100.

The first buffer layer 121 is, like a layer, provided directly on the optical fiber 11 to cover the optical fiber 11. The first buffer layer 121 is made of a resin material such as a thermoplastic resin and a thermosetting resin, and a photocurable resin including an ultraviolet curable resin in one preferred embodiment. In view of excellent processability, the first buffer layer 121 is made of a photocurable resin in one more preferred embodiment, and an ultraviolet curable resin in one far more preferred embodiment. The first buffer layer 121 is made of a fluorine-containing polymer resin, such as a fluorinated acrylate resin, containing fluorine in a molecule in one preferred embodiment.

The first buffer layer 121 may have the following thickness in view of reducing the bending loss when being bent with a small bending diameter without losing flexibility. The thickness falls within a range from 5.0 μm to 40 μm in one preferred embodiment, and from 10 μm to 30 μm in one more preferred embodiment.

The first buffer layer 121 may have the following refractive index (as measured at a wavelength λ of 852 nm and a temperature of 25° C.) in view of reducing the bending loss when being bent with a small bending diameter. The refractive index of the first buffer layer 121 is lower than that of the cladding 112 of the optical fiber 11, and is 1.370 or lower in one preferred embodiment, and 1.360 or lower in one more preferred embodiment. As measured at a wavelength λ of 852 nm and a temperature of 25° C., the difference in the relative refractive index between the core 111 and the first buffer layer 121 of the optical fiber 11 may be as follows. The difference is 5.5% or more in one preferred embodiment, 6.0% or more in one more preferred embodiment, and 6.7% or more in one far more preferred embodiment. The difference in the relative refractive index here is obtained as follows in percentage. The refractive index of the first buffer layer 121 is subtracted from the refractive index of the core 111 of the optical fiber 11. The difference is then divided by the refractive index of the core 111. The obtained value is multiplied by 100.

The first buffer layer 121 has a Shore D hardness of D/20.0/1 or higher. In view of obtaining excellent removability of the jacket 13 without losing flexibility, the first buffer layer 121 may have the following Shore D hardness. The hardness falls within a range from D/20.0/1 to D/100/1 in one preferred embodiment, and from D/30.0/1 to D/80.0/1 in one more preferred embodiment. The Shore D hardness here is measured based on the ASTMD2240 test method at a temperature of 23±2° C. and a testing time of one second (hereinafter, the same).

The second buffer layer 122 is, like a layer, provided directly on the first buffer layer 121 to cover the first buffer layer 121. The second buffer layer 122 is made of a resin material such as a thermoplastic resin and a thermosetting resin, and a photocurable resin including an ultraviolet curable resin in one preferred embodiment. In view of excellent processability, the second buffer layer 122 made of a photocurable resin in one more preferred embodiment, and an ultraviolet curable resin in one far more preferred embodiment. The first buffer layer 121 is made of a fluorine-containing polymer resin, such as a fluorinated acrylate resin, containing fluorine in a molecule in one preferred embodiment.

The second buffer layers 122 may have the following thickness in view of obtaining excellent removability of the jacket 13 without losing flexibility. The thickness falls within a range from 10 μm to 50 μm in one preferred embodiment, and from 15 μm to 40 μm in one more preferred embodiment. The thicknesses of the first buffer layer and the second buffer layer 122 may be the same or different.

The second buffer layer 122 has a refractive index of 1.450 or lower in one preferred embodiment, and 1.420 or lower in one more preferred embodiment (as measured at a wavelength λ of 589 nm and a temperature of 25° C.).

The second buffer layer 122 may have the following Shore D hardness in view of obtaining excellent removability of the jacket 13 without losing flexibility. The hardness falls within a range from D/40.0/1 to D/100/1 in one preferred embodiment, and from D/50.0/1 to D/80.0/1 in one more preferred embodiment. The second buffer layer 122 has a higher Shore D hardness than the first buffer layer 121 has. The difference falls within a range from 10.0 to 70.0 in one preferred embodiment, and from 20.0 to 50.0 in one more preferred embodiment in view of obtaining excellent removability of the jacket 13. The ratio of the Shore D hardness between the first and second buffer layers 121 and 122 (Shore D hardness of the second buffer layer 122/Shore D hardness of the first buffer layer 121) is as follows in view of obtaining excellent removability of the jacket 13. The ratio falls within a range from 1.25 to 2.70 in one preferred embodiment, and from 1.50 to 2.40 in one more preferred embodiment.

The jacket 13 is, like a layer, provided directly on the second buffer layer 122 to cover the second buffer layer 122. The jacket 13 is made of a resin material such as a thermoplastic resin or a thermosetting resin in one preferred embodiment. The jacket 13 is made of a fluorine-based thermoplastic resin containing fluorine in a molecule in one preferred embodiment in view of obtaining excellent removability. Examples of such a fluorine-based resin include a polytetrafluoroethylene (PTFE) resin, an ethylene tetrafluoroethylene copolymer (ETFE) resin, a polychlorotrifluoroethylene (PCTFE) resin, a polyvinylidene fluoride (PVDF) resin, and a polyvinyl fluoride (PVF) resin. Among these, an ethylene tetrafluoroethylene copolymer (ETFE) resin is selected in one preferred embodiment.

The jacket 13 may have the following thickness in view of obtaining excellent removability of the jacket 13 without losing flexibility. The thickness falls within a range from 0.030 mm to 0.30 mm in one preferred embodiment, and from 0.040 mm to 0.20 mm in one more preferred embodiment.

The jacket 13 may have the following Shore D hardness in view of obtaining excellent removability of the jacket 13 without losing flexibility. The hardness falls within a range from D/50.0/1 to D/110/1 in one preferred embodiment, and from D/65.0/1 to D/90.0/1 in one more preferred embodiment. The jacket 13 has a slightly higher Shore D hardness than the second buffer layer 122 in one preferred embodiment. The difference falls within a range from 3.00 to 30.0 in one preferred embodiment, and from 5.00 to 10.0 in one more preferred embodiment in view of obtaining excellent removability of the jacket 13. The ratio of the Shore D hardness between the jacket 13 and the second buffer layer 122 (Shore D hardness of the jacket 13/Shore D hardness of the second buffer layer 122) is as follows in view of obtaining excellent removability of the jacket 13. The ratio falls within a range from 1.04 to 1.75 in one preferred embodiment, and from 1.07 to 1.40 in one more preferred embodiment.

If a coated optical fiber used for treatment of crushing a urinary or kidney stone by irradiation with a laser beam is bent with a small bending diameter in a human body, a high bending loss occurs. If the irradiation of the laser beam continues in this state, leakage light may burn out a resin jacket that covers the optical fiber. There is also a coated optical fiber that includes a resin buffer layer between an optical fiber and a jacket. In a coated optical fiber with such a structure, the buffer layer is retained and only the jacket is removed in one preferred embodiment in view of processability of one end to be attached to, for example, an optical connector.

By contrast, the coated optical fiber 10 according to the embodiment has the structure described above. That is, the first buffer layer 121 as the inner layer and the second buffer layer 122 as the outer layer are provided between the optical fiber 11 and the jacket 13. The first buffer layer 121 has a lower refractive index than that of the cladding 112 of the optical fiber 11. Although light leaks from the core 111 when the coated optical fiber 10 is bent with a small bending diameter, the lower refractive index of the first buffer layer 121 serves as follows. The light, which has leaked from the core 111, is transmitted to an output end, while being confined inside the first buffer layer 121. This substantially reduces the bending loss. The first buffer layer 121 has a Shore D hardness of D/20.0/1 or higher, and the second buffer layer 122 is higher in Shore D hardness than the first buffer layer 121. This leads to excellent removability of the jacket 13, and facilitates the removal of the jacket 13, while retaining the first buffer layer and the second buffer layer 122.

The coated optical fiber 10 according to the embodiment can be manufactured as follows. The optical fiber 11 is drawn from a base material of quartz. An ultraviolet curing resin is applied to the outer peripheral surface of the optical fiber 11, and irradiated with an ultraviolet ray to be cured. The first and second buffer layers 121 and 122 are continuously formed on the resin. The fiber is once wound up, and then passes through an extruder to form the jacket 13.

EXAMPLES

Fluorinated Acrylate Resin

Four types of fluorinated acrylate resins: resins 1 to 4 were prepared. The respective configurations are shown in Table 1.

<Resin 1>
Resin 1 was an ultraviolet curable fluorinated acrylate resin with a post-cure refractive index of 1.340 (as measured at a wavelength λ of 852 nm and a temperature of 25° C.) and a Shore D hardness of D/12.5/1.

<Resin 2>
Resin 2 was an ultraviolet curable fluorinated acrylate resin with a post-cure refractive index of 1.349 (as measured at a wavelength λ of 852 nm and a temperature of 25° C.) and a Shore D hardness of D/37.5/1.

<Resin 3>
Resin 3 was an ultraviolet curable fluorinated acrylate resin with a post-cure refractive index of 1.363 (as measured at a wavelength λ of 852 nm and a temperature of 25° C.) and a Shore D hardness of D/40.0/1.

<Resin 4>
Resin 4 was an ultraviolet curable fluorinated acrylate resin with a post-cure refractive index of 1.402 (as measured at a wavelength λ of 589 nm and a temperature of 25° C.) and a Shore D hardness of D/64.0/1.

TABLE 1

|  | Resin 1 | Resin 2 | Resin 3 | Resin 4 |
| --- | --- | --- | --- | --- |
| Refractive Index | 1.340 | 1.349 | 1.363 | 1.402 |
| Shore D Hardness | D/12.5/1 | D/37.5/1 | D/40.0/1 | D/64.0/1 |

(Coated Optical Fiber)

Coated optical fibers according to Examples 1 and 2 and Comparative Examples were prepared. The respective configurations are shown in Table 2.

Example 1

Example 1 is a coated optical fiber with a structure similar to that of the embodiment. A coated optical fiber was prepared as Example 1 to include a first buffer layer made of the resin 2 and a second buffer layer made of the resin 4.

The coated optical fiber 10 has an outer diameter of 0.43 mm. The optical fiber 11 has an outer diameter of 0.28 mm. The optical fiber includes a core made of pure quartz and having a cross-section with a diameter of 240 μm, and a cladding made of quartz doped with fluorine and having a thickness of 20 μm. As measured at a wavelength λ of 589 nm and a temperature of 25° C., the core has a refractive index of 1.458, while the cladding has a refractive index of 1.441. Accordingly, the difference in relative refractive index between the core and the cladding is 1.2%.

Figure 2:
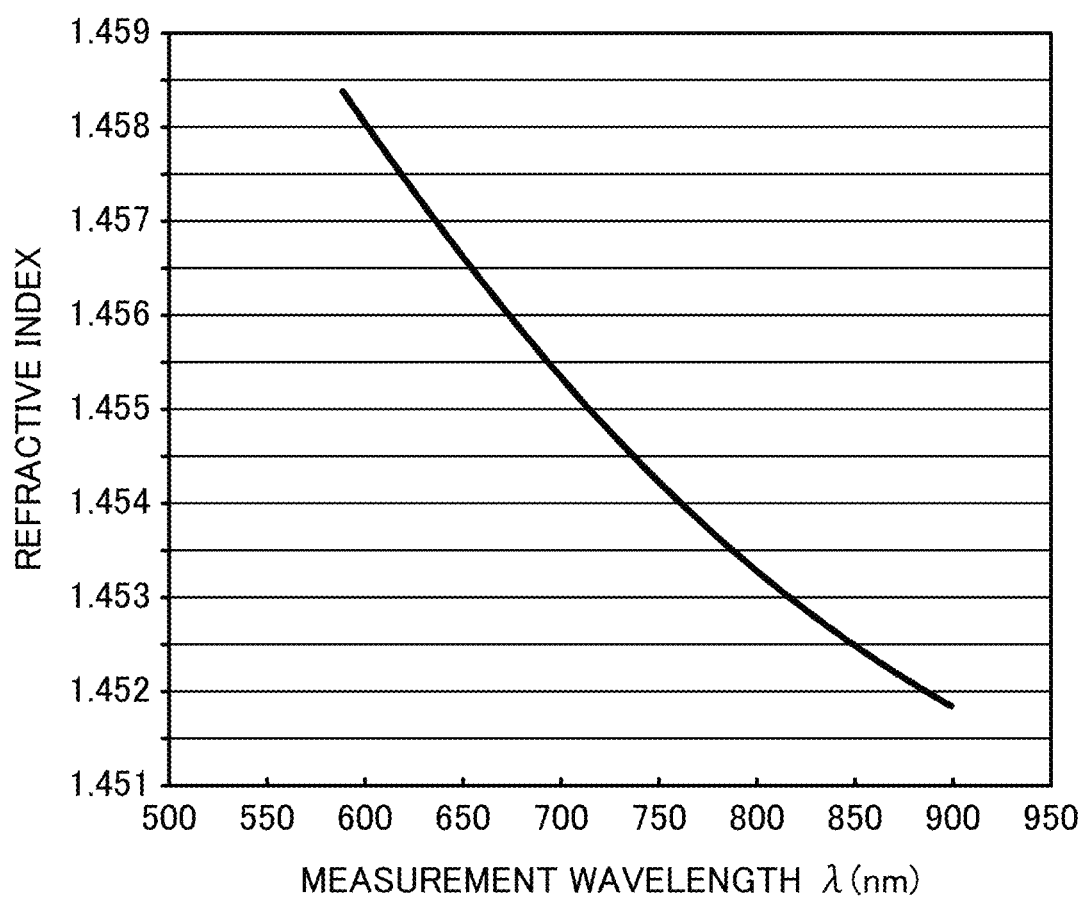
FIG. 2 is a graph illustrating a relationship between a measurement wavelength and a refractive index of pure quartz at 25° C.

FIG. 2 illustrates the relationship between the measurement wavelength λ and the refractive index of pure quartz at 25° C. According to the relationship, the core has a refractive index of 1.452 as measured at a wavelength λ of 852 nm. Therefore, as measured with a wavelength λ of 852 nm at a temperature of 25° C., the difference in the relative refractive index between the core and the first buffer layer is: (1.452−1.349)/1.452≈7.1%.

The first buffer layer had a thickness of 20 μm. The second buffer layer had a thickness of 15 μm. The jacket was made of an ethylene tetrafluoroethylene copolymer (ETFE) resin. The jacket had a thickness of 40 μm. The jacket had a Shore D hardness of D/72.0/1.

Example 2

A first buffer layer is made of the resin 3. Otherwise, the coated optical fiber of Example 2 was prepared as Example 1.

Comparative Example

A first buffer layer is made of the resin 1. Otherwise, the coated optical fiber of Comparative Example was as Example 1.

TABLE 2

|  | Example 1 | Example 2 | Comparative Example |
| --- | --- | --- | --- |
| First Buffer Layer | Resin 2 | Resin 3 | Resin 1 |
| Second Buffer Layer | Resin 4 | Resin 4 | Resin 4 |
| Difference (%) in Relative Refractive Index between Core and First Buffer Layer | 7.1 | 6.1 | 7.7 |
| Difference in Shore D Hardness between First and Second Buffer Layers | 26.5 | 24.0 | 51.5 |
| Ratio of Shore D Hardness between First and Second Buffer Layers | 1.7 | 1.6 | 5.1 |
| Difference in Shore D Hardness between Jacket and Second Buffer Layer | 8.0 | 8.0 | 8.0 |
| Ratio of Shore D Hardness between Jacket and Second Buffer Layer | 1.1 | 1.1 | 1.1 |

(Test Method)

Figure 3:
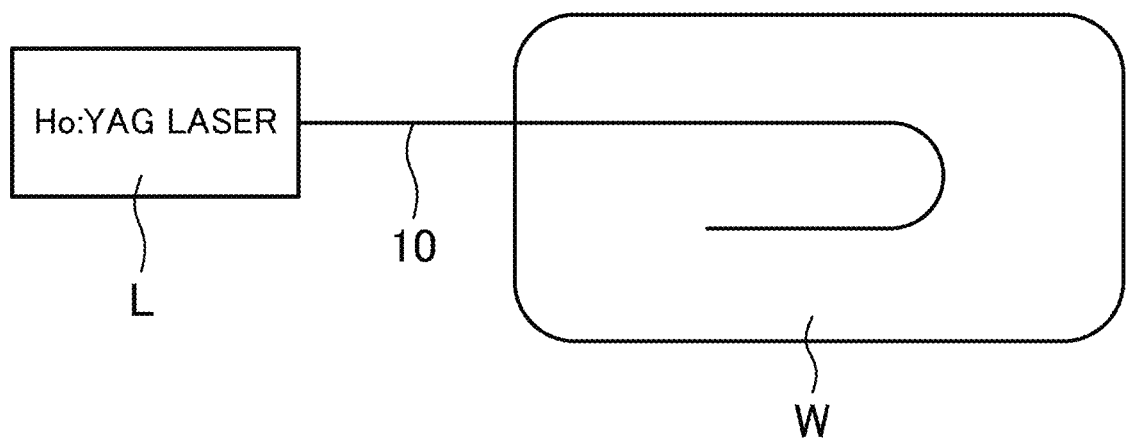
FIG. 3 illustrates a test method for determining a burnout rate.

<Burnout Rate>
For each of the coated optical fibers of Examples 1 and 2 and Comparative Example, the burnout rate was tested as follows. As shown in FIG. 3, each coated optical fiber 10 was bent into a U-shape with a bending diameter of 1.5 cm, with one end connected to a Ho:YAG laser L and the other end immersed in water W. In this state, the Ho:YAG laser L outputted a pulse laser beam with an energy of 1.5 J per pulse and a wavelength of 2.1 μm at a frequency of 30 Hz for one minute (with an average output of 45 W). At this time, the presence or absence of damage, such as disconnection, of the optical fiber was confirmed. This trial was performed 20 times, and the percentage of the number of trials, in which damage was confirmed, was evaluated as the burnout rate. A similar test was also performed, where the coated optical fiber was bent into a U shape with a bending diameter of 1.0 cm.

<Removability of Jacket>

For each of the coated optical fibers of Examples 1 and 2 and Comparative Example, the jacket removability was tested as follows. With the use of a jacket stripping tool (manufactured by Micro Electronics), the jacket with a length of 5 cm from the end of the coated optical fiber was removed. The presence or absence of damage of the exposed second buffer layer was confirmed. Then, the case without any damage was evaluated as A, while the case with damage was evaluated as B.

(Test Results)

The test results are shown in Table 3.

TABLE 3

|  | Example 1 | Example 2 | Comparative Example |
|---|---|---|---|
| Burnout Rate % (Bending Diameter of 1.5 cm) | 0 | 5 | 0 |
| Burnout Rate % (Bending Diameter of 1.0 cm) | 0 | 0 | 0 |
| Jacket Removability | A | A | B |

It is apparent from Table 3 that Examples 1 and 2 with the following features exhibit a low burnout rate and excellent jacket removability. The first buffer layer has a refractive index lower than that of the cladding. The first buffer layer has a Shore D hardness of D/20.0/1 or higher. The second buffer layer has a Shore D hardness higher than that of the first buffer layer.

On the other hand, it is apparent that Comparative Example with the following features exhibits a low burnout rate but less jacket removability. The first buffer layer has a refractive index lower than that of the cladding refractive index than the cladding. The second buffer layer has a Shore D hardness harder than that of the first buffer layer. However, the first buffer layer has a Shore D hardness lower than D/20.0/1.

INDUSTRIAL APPLICABILITY

The present invention is useful in the technical field of coated optical fibers.

DESCRIPTION OF REFERENCE CHARACTERS

10 Coated Optical Fiber
11 Optical Fiber
111 Core
112 Cladding
121 First Buffer Layer
122 Second Buffer Layer
13 Jacket

What is claimed is:

1. A coated optical fiber, comprising:
    an optical fiber including a core, and a cladding covering the core, said cladding having a refractive index lower than a refractive index of the core;
    a first buffer layer covering the optical fiber, said first buffering layer comprising an ultraviolet curable fluorinated acrylic resin having a post-cure refractive index lower than the refractive index of the cladding and a Shore D hardness of D/20.0/1 or higher, wherein a difference in relative refractive index between the core and the first buffer layer is in a range from 5.5% to 7.1%;
    a second buffer layer covering the first buffer layer, said second buffer layer comprising an ultraviolet curable fluorinated acrylic resin in a tubular resin layer, and having a Shore D hardness higher than the Shore D hardness of the first buffer layer, wherein a ratio of Shore D hardness between the first buffer layer and the second buffer layer is in a range of 1.5 to 2.4; and
    a jacket covering the second buffer layer, said jacket comprising a fluorine-based thermoplastic resin having a Shore D hardness higher than the Shore D hardness of the second buffer layer, the Shore D hardness of the jacket being in a range from D/50.0/1 to D/110/1,
    wherein the first and the second buffer layers are formed over the entire length of the optical fiber, and
    wherein the jacket is provided directly on the second buffer layer.

2. The coated optical fiber according to claim 1, wherein a difference in the Shore D hardness between the second buffer layer and the first buffer layer falls within a range from 10.0 to 70.0.

3. The coated optical fiber according to claim 1, wherein the jacket has the Shore D hardness higher than the Shore D hardness of the second buffer layer.

4. The coated optical fiber according to claim 3, wherein a difference in the Shore D hardness between the jacket and the second buffer layer falls within a range from 3.00 to 30.0.

5. The coated optical fiber, according to claim 1, used for endoscope equipment.

6. The coated optical fiber according to claim 1, wherein the jacket is made of an ETFE.

7. The coated optical fiber according to claim 1, wherein:
    the thickness of the first buffer layer ranges from 5 μm to 40 μm,
    the thickness of the second buffer layer ranges from 10 μm to 50 μm, and
    the thickness of the jacket ranges from 0.03 mm to 0.3 mm.

* * * * *

UNITED STATES PATENT AND TRADEMARK OFFICE
CERTIFICATE OF CORRECTION

PATENT NO. : 11,385,431 B2
APPLICATION NO. : 16/474504
DATED : July 12, 2022
INVENTOR(S) : Masatoshi Tanaka et al.

Page 1 of 1

It is certified that error appears in the above-identified patent and that said Letters Patent is hereby corrected as shown below:

On the Title Page

Column 1, Line 1, under Assignee, delete "Mitshishi" and insert --Mitsubishi--.

In the Specification

In Column 2, Line 5 (Approx.), delete "10according" and insert --10 according--.

In the Claims

In Column 8, Claim 5, Line 42 (Approx.), delete "fiber," and insert --fiber--.

Signed and Sealed this
Twenty-fourth Day of January, 2023

Katherine Kelly Vidal
*Director of the United States Patent and Trademark Office*